(12) United States Patent
Hua et al.

(10) Patent No.: US 10,064,545 B2
(45) Date of Patent: Sep. 4, 2018

(54) MULTI-RESOLUTION FOVEATED ENDOSCOPE/LAPAROSCOPE

(71) Applicant: The Arizona Board of Regents on behalf of the University of Arizona, Tucson, AZ (US)

(72) Inventors: Hong Hua, Tuscon, AZ (US); Yi Qin, Tucson, AZ (US); Mike Nguyen, La Canada, CA (US)

(73) Assignee: THE ARIZONA BOARD OF REGENTS ON BEHALF OF THE UNIVERSITY OF ARIZONA, Tucson, AZ (US)

( * ) Notice: Subject to any disclaimer, the term of this patent is extended or adjusted under 35 U.S.C. 154(b) by 452 days.

(21) Appl. No.: 14/436,321

(22) PCT Filed: Oct. 18, 2013

(86) PCT No.: PCT/US2013/065767
§ 371 (c)(1),
(2) Date: Apr. 16, 2015

(87) PCT Pub. No.: WO2014/063106
PCT Pub. Date: Apr. 24, 2014

(65) Prior Publication Data
US 2015/0238071 A1    Aug. 27, 2015

Related U.S. Application Data

(60) Provisional application No. 61/795,509, filed on Oct. 18, 2012.

(51) Int. Cl.
*A61B 1/00* (2006.01)
*A61B 1/04* (2006.01)
(Continued)

(52) U.S. Cl.
CPC ............ *A61B 1/07* (2013.01); *A61B 1/00096* (2013.01); *A61B 1/00172* (2013.01);
(Continued)

(58) Field of Classification Search
CPC ............ A61B 1/00096; A61B 1/00172; A61B 1/00188; A61B 1/04; A61B 1/00193;
(Continued)

(56) References Cited

U.S. PATENT DOCUMENTS 5,836,869 A * 11/1998 Kudo ................. A61B 1/00039
600/102
5,846,185 A   12/1998 Carollo et al.
(Continued)

FOREIGN PATENT DOCUMENTS

WO    2014048972    4/2014
WO    2014147060    9/2014

OTHER PUBLICATIONS

Qin et al., Multi-resolution foveated laparoscope with high resolvability, Optics Letters, 2013, 2191-2193, 38(13).
(Continued)

*Primary Examiner* — Timothy J Neal
*Assistant Examiner* — Aaron B Fairchild
(74) *Attorney, Agent, or Firm* — Niels Haun; Dann, Dorfman, Herrell & Skillman, P.C.

(57) ABSTRACT

A multi-resolution foveated laparoscope (MRFL) addresses a number of the clinical limitations described in the background section. The MRFL technology can (1) simultaneously obtain both wide-angle- and high-magnification images of a surgical area in real-time in a single, fully integrated scope, (2) yield ultra-high spatial resolution which is over 3 times better than a standard laparoscope (SL) at a close-up working distance, (3) automatically scan and engage the high-magnification imaging probe to any sub-
(Continued)

region of the surgical field through region-of-interest (ROI) tracking capabilities, (4) vary the optical magnification of the high-resolution imaging probe without the need of physically advancing or withdrawing the scope, (5) maintain a low-length profile, optimized for operating at a long working distance (WD), providing both superb spatial awareness and high-magnification views simultaneously. It allows the scope to be secured to the camera port with reduced conflicts with other surgical instruments in single port access procedures (SPA).

32 Claims, 11 Drawing Sheets

(51) Int. Cl.
   A61B 1/06      (2006.01)
   A61B 1/07      (2006.01)
   A61B 1/313     (2006.01)
   A61B 1/045     (2006.01)

(52) U.S. Cl.
   CPC .......... *A61B 1/00188* (2013.01); *A61B 1/042* (2013.01); *A61B 1/045* (2013.01); *A61B 1/0669* (2013.01); *A61B 1/0684* (2013.01); *A61B 1/3132* (2013.01)

(58) Field of Classification Search
   CPC ............ A61B 1/00163; A61B 1/00165; A61B 1/00071; A61B 1/0684; A61B 1/3132; G02B 23/2453
   USPC ....................................................... 600/138
   See application file for complete search history.

(56) References Cited

U.S. PATENT DOCUMENTS

| | | | |
|---|---|---|---|
| 6,007,484 A * | 12/1999 | Thompson | A61B 1/00096 600/122 |
| 6,236,513 B1 | 5/2001 | Mallary | |
| 7,267,647 B2 | 9/2007 | Okada et al. | |
| 7,455,638 B2 | 11/2008 | Ogawa et al. | |
| 7,942,810 B2 | 5/2011 | Uchimura et al. | |
| 8,262,559 B2 | 9/2012 | Krattiger | |
| 2001/0023314 A1 | 9/2001 | Bodor | |
| 2002/0057341 A1* | 5/2002 | Tanaka | A61B 1/00045 348/143 |
| 2002/0091325 A1 | 7/2002 | Ostrovsky | |
| 2004/0189799 A1* | 9/2004 | Spencer | A61B 1/00188 348/85 |
| 2006/0114986 A1* | 6/2006 | Knapp, II | A61B 1/00103 375/240.01 |
| 2006/0293562 A1 | 12/2006 | Uchimura et al. | |
| 2007/0149858 A1 | 6/2007 | Ogawa | |
| 2008/0018734 A1 | 1/2008 | Iriyama | |
| 2009/0259098 A1 | 10/2009 | Krattiger | |
| 2010/0165485 A1 | 7/2010 | Do | |
| 2010/0174144 A1* | 7/2010 | Hsu | A61B 1/00087 600/122 |
| 2010/0210937 A1 | 8/2010 | Tearney et al. | |
| 2013/0237762 A1 | 9/2013 | Fengler | |

OTHER PUBLICATIONS

Hua et al., Multi-resolution foveated laparoscope for safer minimally invasive surgery, SPIE, 2013, 1-4.

Rogers et al., Foveated endoscope objective design to combine high resolution with wide field of view. BIOS. International Society for Optics and Photonics, 2010.

Sekiya et al. Development of a dual-view endoscope system. Biomedical Optics 2006. International Society for Optics and Photonics, 2006.

Qin et al. Development of a laparoscope with multi-resolution foveation capability for minimally invasive surgery. SPIE SiOS. International Society for Optics and Photonics, 2013.

Hagan et al., Foveated endoscopic lens. Journal of Biomedical Optics 17.2 (2012) 0211041-0211046.

Notification of Transmittal of the International Search Report and the Written Opinion of the International Searching Authority, or the Declaration for Int'l Application No. PCT/US2013/065767 dated Jan. 22, 2014, 13 pages.

International Search Report dated Jun. 3, 2016 for application PCT/US2016/013657.

* cited by examiner

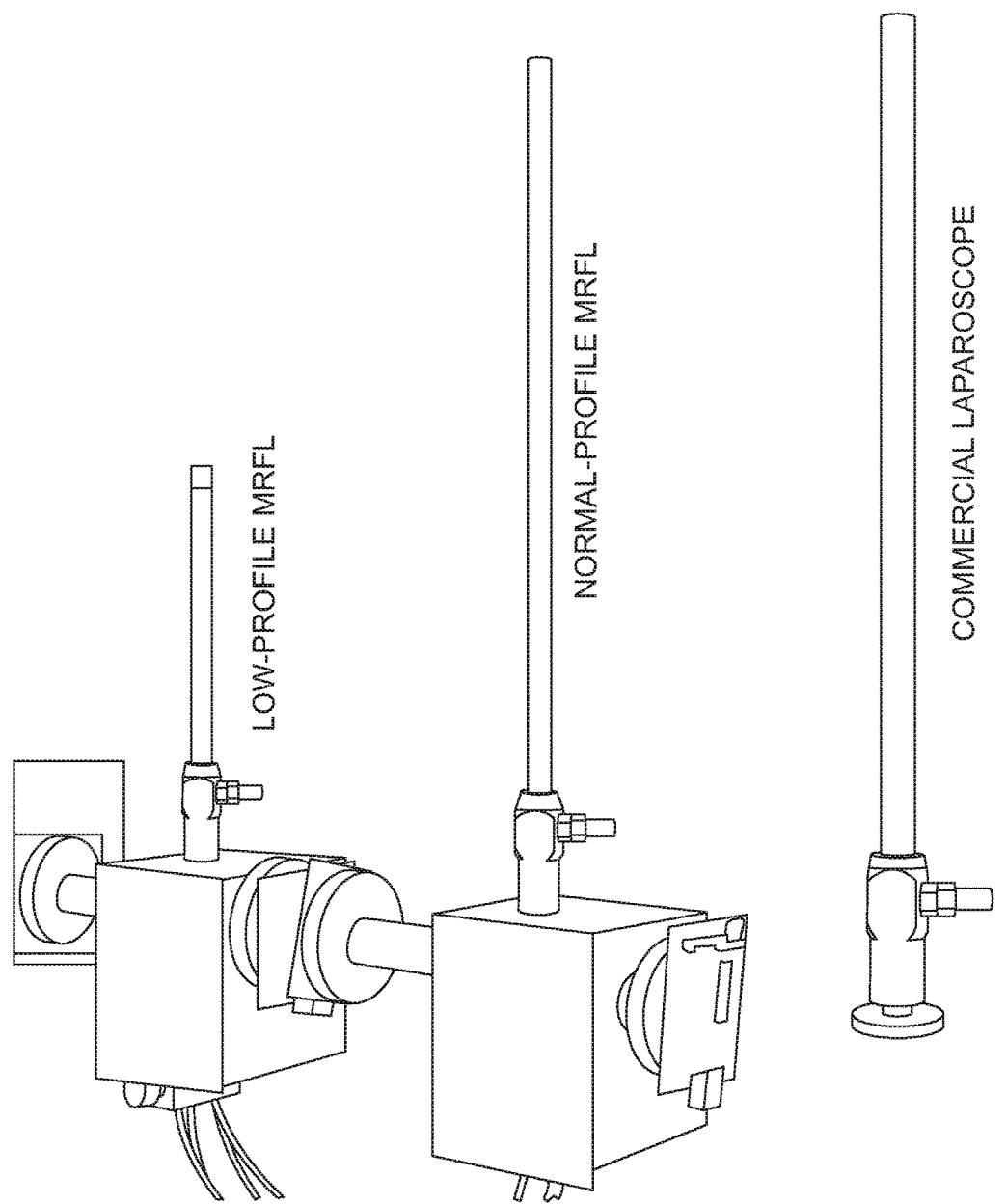

Wide-Angle Image

High-Magnification Image

MULTI-RESOLUTION FOVEATED ENDOSCOPE/LAPAROSCOPE

CROSS-REFERENCE TO RELATED APPLICATION

This application claims priority to and receives the benefit of U.S. Provisional Patent Application No. 61/795,509, filed Oct. 18, 2012, which application is incorporated herein in its entirety by this reference.

This invention was made with government support under Grant No. R21 EB013370 awarded by the National Institutes of Health. The government has certain rights in the invention.

BACKGROUND OF THE INVENTION

Laparoscopy has been the most successful means of providing minimally invasive surgery (MIS) procedures and routinely performed in several surgical fields for procedures such as cholecystectomy, appendectomy, hysterectomy, and nephrectomy. It has a number of well-recognized advantages to the patient versus an open procedure, including reduced pain, shorter recovery time and hospital stay time, and reduced cost. It has become the gold standard approach for several procedures including cholecystectomy (96% of 1.06 million cases performed laparoscopically in 2011 in the United States) and appendectomy (75% of 359,000 cases performed laparoscopically in 2011).

The current laparoscopic technologies suffer a number of major limitations, one of which is a tradeoff of limited field of view (FOV) for high spatial resolution versus wide FOV for situational awareness but with diminished resolution. Standard laparoscopes (SL) lack the ability to acquire both wide-angle and high-resolution images simultaneously through a single scope. This limitation introduces challenges when used in clinical scenarios requiring both close-up views for details and wide-angle overviews for orientation and situational awareness during surgical maneuvers. With a SL, in order to see fine details of a surgical field, procedures must usually be performed at a highly zoomed-in view, where the scope is moved in to operate at a short working distance (WD), typically less than 50 mm. A highly zoomed-in view leads to the loss of peripheral vision and awareness of potentially dangerous situations occurring outside the immediate focus area of the laparoscope. One example occurs when a non-insulated laparoscopic instrument is in inadvertent and unrecognized contact with an energized instrument resulting in spread of electric current being applied to unintended structures, a situation known as "direct coupling". Insulation failures in energized instruments themselves can also directly lead to injury to bowel, vascular, and other structures. These injuries often remain unrecognized if they occur on the part of the surgical instrument that is not within the FOV of the laparoscope. While literature documenting inadvertent injuries in laparoscopic surgery are likely underreported, the Association of Trial Lawyers of America has stated that "During laparoscopic monopolar electrosurgery, most electrosurgical burns are not detected at the time of surgery because they occur outside of the surgeon's keyhole field of view", reinforcing the seriousness of this issue. Single port access procedures (SPA), where surgical instruments and the laparoscope are all placed through a single combined trocar, have been introduced to further reduce the invasiveness of MIS procedures, may play a larger role in the future of laparoscopic surgery. SPA procedures further increase the concerns for inadvertent electrosurgical injuries because the close proximity of instruments in a single port leads to the frequent crossing of instruments out of the surgeons view. This results in a higher potential for injuries from direct coupling of instruments or from unrecognized breaks in instrument insulation causing injury to adjacent tissue.

In the current clinical practice, the FOV limitation is addressed by manually moving the entire laparoscope in and out of the camera port to obtain either close-up views for details or wide-angle overviews for orientation. This practice requires a trained assistant for holding and maneuvering the camera. The practice of frequently maneuvering the camera using a trained assistant can introduce ergonomic conflicts with hand cross-over between the surgeon and the assistant holding the camera, which imposes an inherent challenge to laparoscopic procedures. The ergonomic conflicts associated with standard laparoscopy are aggravated with the SPA approach. Port-grouping in SPA procedures raised a number of challenges, including tunnel vision due to the in-line arrangement of instruments, poor triangulation of instruments, requiring crossing of instruments to obtain proper retraction, and increased risk of instrument collision due to the close proximity of the laparoscope to other surgical devices. It demands further refinement of laparoscopic instrumentation to address these limitations and optimize surgical task performance.

To overcome the FOV and ergonomic limitations of standard laparoscopy, robotically assisted techniques, such as voice, foot pedal, or head motion-activated cameras, have been developed to eliminate the need for a human camera holder. However, delays in task performance have been reported due to errors in voice recognition or robotic control of camera speed, and also significant practice is required to become efficient with set-up and use. There have also been prior attempts to create cameras that have a low external profile with HD picture and automatic focusing. These scopes, however, still require advancing and withdrawing of the lens to obtain magnification, which can lead to problems with inadvertent and restricted movement of the laparoscope due to collisions with other instruments internally and issues with hand collisions externally. It has also been suggested that varying the magnification of the laparoscope and making it a low profile could reduce the effect of crowding, but this approach alone could compound the problem of loss of situational awareness from zoomed-in surgery. A better approach to laparoscopic imaging which balances high spatial resolution with preservation of situational awareness is needed. This solution would also need to minimize the ergonomic conflicts and healthcare costs which arise from the requirement to frequently maneuver a bulky laparoscope using a trained assistant.

It is therefore desirable to provide improved laparoscopes and other types of scopes and methods of using them, where the above short comings are alleviated.

SUMMARY OF THE INVENTION

One embodiment is directed to an endoscope comprising an inserting tube having a viewing end and a distal end, where the distal end is suitable to be inserted into a human body to a location next to a region in the human body to be viewed. A first optical system in the inserting tube is employed for transmitting light originating from the region from the distal end towards the viewing end. A second optical system employed at or near the viewing end splits the light transmitted by the first optical system along two different first and second optical paths. A first imaging probe in the first optical path images the region at a first field of view and at a first magnification. A second imaging probe in the second optical path images a subregion in the region at a second field of view that is smaller than the first field of view and at a second magnification that is higher than the first magnification.

Another embodiment is directed to an endoscope comprising an inserting tube having a viewing end and a distal end, where the distal end is suitable to be inserted into a human body to a location next to a region in the human body to be viewed. A first optical system in the inserting tube transmits light originating from the region from the distal end towards the viewing end. A second optical system at or near the viewing end splits the light transmitted by the first optical system along two different first and second optical paths to provide views of the region or a subregion thereof at two different fields of view and at two different magnifications. A plurality of LEDs emit light. The inserting tube includes a third optical path transmitting light emitted by the LEDs to illuminate the region in the human body to be viewed.

Yet another embodiment is directed to a method for viewing a region in the human body, comprising inserting into the human body a tube having a viewing end and a distal end, so that the distal end is located next to a region in the human body to be viewed. Light originating from the region is transmitted from the distal end towards the viewing end. The light transmitted towards the viewing end is split along two different first and second optical paths. The light transmitted along the first optical path is directed to a first imaging sensor for imaging the region at a first field of view and at a first magnification. The light transmitted along the second optical path is directed to a second imaging sensor for imaging a subregion within the region at a second field of view that is smaller than the first field of view and at a second magnification that is higher than the first magnification, to provide a foveated image of the subregion, wherein the region and subregion are imaged at substantially the same time.

All patents, patent applications, articles, books, specifications, other publications, documents and things referenced herein are hereby incorporated herein by this reference in their entirety for all purposes. To the extent of any inconsistency or conflict in the definition or use of a term between any of the incorporated publications, documents or things and the text of the present document, the definition or use of the term in the present document shall prevail.

BRIEF DESCRIPTION OF THE DRAWINGS

FIG. 9 shows two integrated prototypes of different length profile scope: a normal profile and a low profile, and of a commercial scope for comparison.

For simplicity in description, identical components are labeled by the same numerals in this Application.

DETAILED DESCRIPTION OF EXEMPLARY EMBODIMENTS

Figures 1A, 1B:
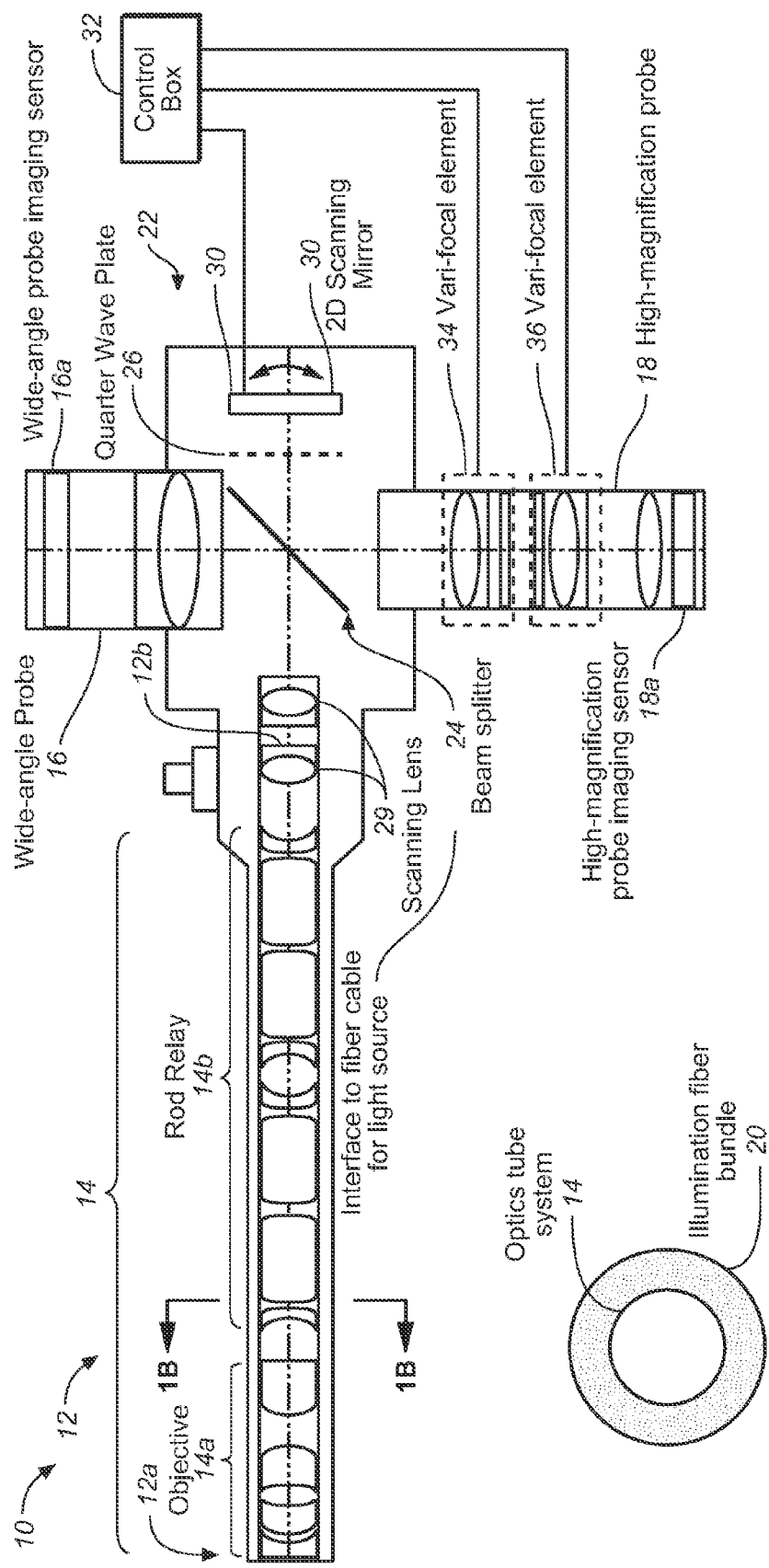
FIG. 1A is a schematic view of a laparoscope to illustrate a first embodiment of the invention.
FIG. 1B is a cross-sectional view of inserting tube 12 of the laparoscope of FIG. 1A along the line 1B-1B in FIG. 1A.

We developed a multi-resolution foveated laparoscope (MRFL) aiming to address a number of the clinical limitations described in the background section. The MRFL technology can (1) simultaneously obtain both wide-angle- and high-magnification images of a surgical area in real-time in a single, fully integrated scope, (2) yield ultra-high spatial resolution which is over 3 times better than a SL at a close-up working distance, (3) automatically scan and engage the high-magnification imaging probe to any subregion of the surgical field through region-of-interest (ROI) tracking capabilities, (4) vary the optical magnification of the high-resolution imaging probe without the need of physically advancing or withdrawing the scope, (5) maintain a low-length profile, optimized for operating at a long WD, providing both superb spatial awareness and high-magnification views simultaneously. It allows the scope to be secured to the camera port with reduced conflicts with other surgical instruments in SPA procedures.

The MRFL technology will provide important new surgical tools and widespread impacts. Because of the unique spatial awareness and resolution advantages of our imaging method, such a system can be quickly translated to several fields of clinical use. First, integrating multi-resolution devices into a single scope will simultaneously provide the ability to survey a large surgical field and to visualize a targeted area in high spatial resolvability for surgical treatment. Concurrent access to both imaging scales in real time offers un-compromised context and resolution, which is expected to offer improved situational awareness and therefore better patient safety and surgical outcome. Secondly, the technology will provide surgeons much more flexibility in terms of scope positioning than what a fixed-magnification laparoscope can provide. The foveated scope provides much improved spatial resolution and enables highly resolvable visualization of tissues and thus enhances intro-operative surgical decision making. It is thus expected to enable enhanced surgical technique, accuracy, and potentially reduce operation time. Thirdly, automated ROI tracking and zooming capabilities will allow for operation without requiring a dedicated assistant or robotic arm to maneuver the scope, and will also minimize camera maneuvering, thereby reducing interference with other surgical instruments in the laparoscopic field. The low profile characteristics of the scope could minimize physical interference between instruments in SPA procedures. Fourthly, the technology not only represents a significant complement to the current laparoscopic procedures, but will also enable other clinical applications. For instance, endoscopy has been recently applied to high-resolution microscopic imaging for screening and assessment of early-stage diseases. When combined with a number of optically active contrast agents and further tuning to the design parameters, the MRFL technology can be enhanced with the ability to capture microscopic image embedded in a wide-FOV imaging probe and may be applied to high-resolution molecular imaging for early-stage cancer screening and for rapid evaluation of the effectiveness of targeted therapeutic treatment, enabling new ways of diagnosing and characterizing disease.

Overall, the technology may have broad impact in surgical practice as laparoscopic approaches have quickly supplanted traditional open surgery. In the case of cholecystectomies, adoption of laparoscopic surgery grew from 2.5% to 76.6% between 1988 and 1997 with an even higher rate expected currently. By facilitating standard laparoscopy and particularly single port access surgical approaches, a broad population of patients may benefit from this project. Single port access in particular has been widely adopted in a number of surgical specialties and for various surgical applications. Reported applications include general surgery (cholecystectomy, appendectomy, hernia repair); urology (nephrectomy, pyeloplasty); obstetrics and gynecology (hysterectomy); and pediatric surgery (diaphragmatic hernia repair).

Innovation

The MRFL technology captures both wide-angle and high-magnification images of a surgical area in real time at variable optical magnifications. This was accomplished by employing a foveated imaging approach in analogy to the human visual system, where a wide-angle imaging probe images the big context (i.e. the peripheral vision) and a high-magnification imaging probe is steered toward a region of interest (i.e. foveation vision). Analogous to eye movement tracking and eye lens accommodation capabilities, the system is capable of automatically tracking and engaging the high-magnification imaging probe to any sub-region of a surgical field and adjusting its optical magnification to a task-appropriate scale without the need of physically moving the imaging probe. The MRFL approach is innovative in that it optically couples a wide FOV laparoscope probe with an actively foveated, high-resolution imaging probe with continuously adjustable ROI and magnification. It preserves the benefits of a wide FOV and enhances a low-resolution imaging probe with high-resolution imaging probe. Although providing significantly advanced imaging capabilities, the multi-resolution imaging probe preserves the compactness of a standard laparoscope. The MRFL approach not only represents an innovative design of a medical imaging probe and significant improvements to current laparoscopic technologies, but also represents a potential to shift the current clinical practice with laparoscopic procedures.

Overview

FIG. 1A illustrates a schematic layout of the MRFL system. The laparoscope 10 comprises an inserting tube 12 with a distal end 12a and a viewing end 12b. Distal end 12a is suitable for insertion into a cavity or incision of a human or animal body (not shown) and placed at a location adjacent or next to an area of interest (not shown) that is to be inspected by viewing. The terms "area of interest" and "region of interest (ROI) are used interchangeably in this document. Tube 12 contains therein first optical system 14 including an objective lens or lens group 14a located at the distal end of the tube and a relay lens component or group 14b that together transmit light from the area of interest to the viewing end 12b. At or near the viewing end 12b, the laparoscope 10 comprises an optical system which includes a wide-angle imaging probe 16 having an imaging sensor 16a, and a high magnification imaging probe 18 having an imaging sensor 18a. The optical system 14 transmits light from the area of interest to two partially shared imaging paths, and then to the two imaging probes to be sensed respectively by two separate image sensors 16a and 18a which will acquire images of respectively the region, and a sub-region within the region, at the same time. The two imaging probes 16 and 18 also fully share an illumination system that is described below in reference to FIG. 2. The two imaging probes share most of the optical components and capture the surgical field of interest from a common viewpoint, which enables seamless registration between the low and high-resolution images. FIG. 1B is a cross-sectional view of inserting tube 12 of the MRFL of FIG. 1A along the line 1B-1B in FIG. 1A. As shown in FIG. 1B, tube 12 contains optical system 14 and illumination fiber bundle 20 that carries light from a light source to illuminate the area of interest adjacent to the distal end of tube 12.

Laparoscope 10 will operate concurrently in both wide- and narrow-angle modes. In the wide-angle mode, the primary sensor 16a will image the entire surgical field with a wide FOV and relatively low spatial resolution, providing a "stadium view", equivalent to those of a standard laparoscope, illustrated in FIG. 10A, where the FOV in this figure shows a target 180 mm away from the distal end 12a. In the high-magnification mode, the secondary sensor 18a will image a sub-region of the stadium view in FIG. 10A (shown within a square box in FIG. 10A), which we call the "foveated" field, at high resolution to visualize more detailed structure for surgical treatment, as illustrated in FIG. 10B. Wide-angle images such as that shown in FIG. 10A will be analyzed with automated image processing tools to identify regions for high-resolution imaging.

Figure 10A:
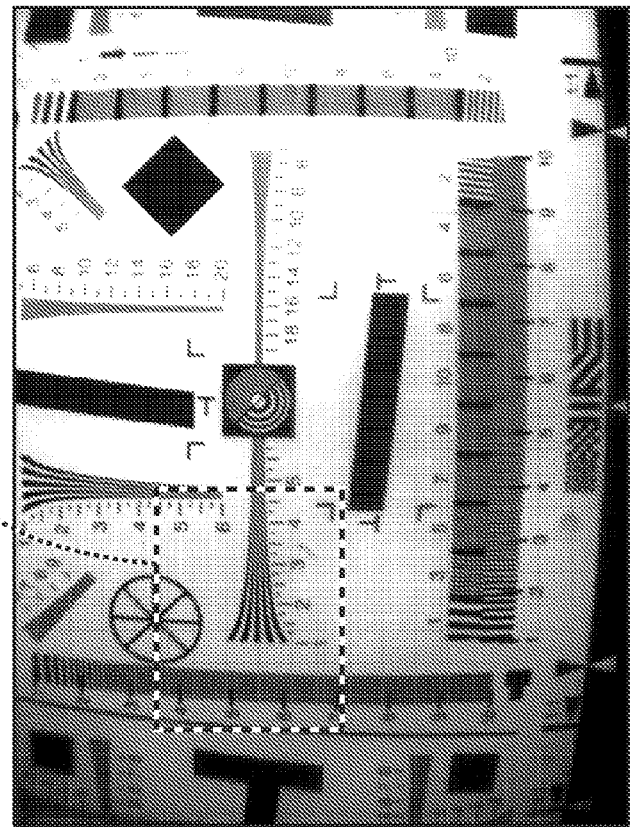
FIGS. 10A and 10b are respectively a wide angle image and a high magnification image of a resolution target taken where the laparoscope in the above embodiments is at a distance of 180 mm from the target.
Figure 10B:
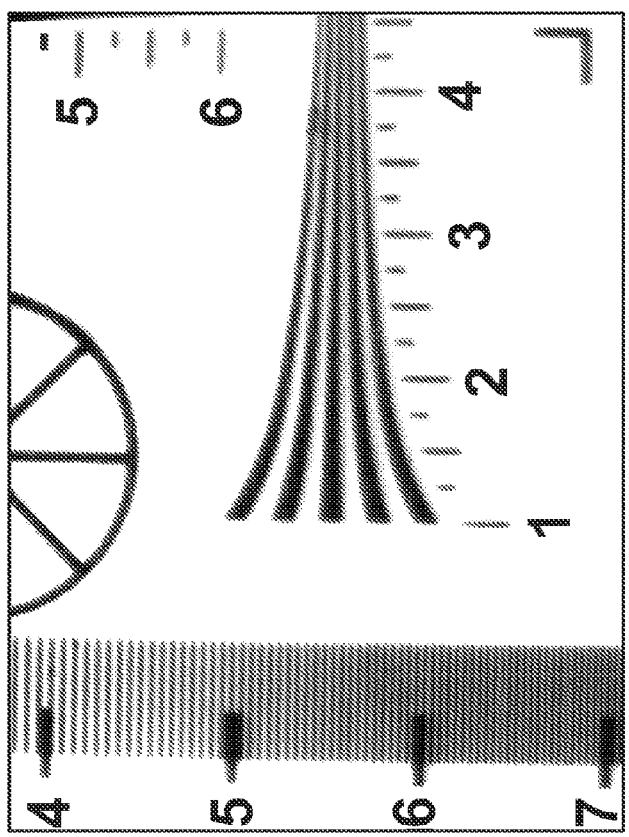

A second optical system 22 including the two imaging probes 16 and 18 is placed at or near the viewing end 12b of the tube 12 to provide the views and images illustrated in FIGS. 10A and 10B. Light from the area of interest collected by objective lens group 14a and relayed by relay lens component 14b is transmitted to the second optical system 22, which includes a beam splitter 24 that reflects to the wide angle imaging probe 16 a portion of the light from relay lens component 14b and transmits a portion of such light which is reflected by scanning mirror 30 and again by beam splitter 24 to the high magnification imaging probe 18. Thus, the beam splitter 24 splits the light transmitted by objective lens group 14a and relayed by relay lens component 14b along two different optical paths: one for wide angle imaging and the other for high-magnification imaging. The second optical system 22 further includes a 2D scanner comprising a scanning lens group 29 and a 2D scanning mirror 30. The 2D scanner steers the light from the optical system 14 such that the high-magnification imaging probe 18 is foveated on a selected region of interest over the field of view imaged by the wide-angle imaging probe 16. Preferably, the beam splitter 24 is a polarizing beam splitter, which reflects S-polarized light and transmits P-polarized light. The P-polarized light is altered by an optional quarter wave plate 26 (shown in dashed line) to become S-polarized and is reflected by polarizing beam splitter 24 to the high magnification imaging probe 18. This approach will increase the amount of light that will be directed to the high magnification imaging probe 18 and is therefore preferable. Since probe 16 has a larger FOV than that of probe 18, more light will enter probe 16 than probe 18 if the beam splitter 24 splits the reflected and transmitted light equally. This may cause the foveated image to be too dim. To compensate for this, the beam splitter 24 may be designed so that the intensity of light transmitted by the beam splitter is at least 1.5 times that of the intensity of light reflected by the beam splitter.

The core of the system 22 will be a high-speed miniature optical scanner 30 that enables foveation and a high-speed optical device that enables a large-range of magnification control without moving parts. In the embodiment of FIG. 1A, we adopt a two-axis MEMS mirror device 30 as a compact, robust scanner which steers and scans the foveated field along two directions transverse to one another in response to a control signal from control device 32 towards subregions of interest to acquire high-resolution images. Thus, in reference to FIGS. 10A and 10B, the control signal can cause the foveated view in FIG. 10B to be moved to a different location within the stadium view in FIG. 10A, and in fact to any desired location within the stadium view in FIG. 10A. The same is true for the embodiments in FIGS. 3 and 4 described below.

A fine adjustment of optical magnification is highly desirable for the foveated probe to obtain high-magnification views with desired field coverage and to provide an optical zoom capability for continuous control on magnification and resolution. It is desirable to achieve continuous zoom to the foveated views without affecting the wide-angle view and the focusing distance in the object space, which shall be fixed once the scope is locked in a position. This requirement imposes a major challenge because varying the optical power for zoom inevitably causes a change of object-image conjugate planes, which results in a change of focusing distance in the object space or a change of detector plane position in the image space. If not appropriately compensated, varying the optical power of the foveated probe alone may cause severe mismatch of focused objects between the wide-angle and foveated probes and cause image blurry to the foveated probe during zooming.

We adopt a variable-focal length element 34, such as a high-speed miniature liquid lens or other tunable lens device, whose focal length may be altered, to thereby allow the optical magnification of the foveated probe to be controlled by varying the applied voltage from control device 32 without any moving parts and without the need to physically advance or withdraw the scope. Additionally, a second variable-focal element (VFE) 36 may be utilized to compensate the focus shift caused by varying the optical power of the first VFE 34 and to maintain the object-image conjugate planes fixed during optical zoom. The foveated field can thus be optically zoomed in conveniently to a much narrower sub-region to visualize fine features which will identify suspicious lesions. The optical magnification of the foveated field is adjustable by controlling the applied voltage from control device 32, covering up to ⅑ of the area covered by the wide-angle sensor, and is capable of providing a spatial resolution at least 3 times better than a standard laparoscope and can be as high as a few microns when high magnification is applied. The ratio between the magnification of the high resolution foveated view and the magnification of the wide angle stadium view achieved in the embodiments of this invention is greater than 2.

The main advantages, compared against a conventional approach with a mechanically moving part, include speed, robustness, and simplicity. After comparing the different VFE technologies such as electrowetting lens, electrophoretic lens, and elastomer-membrane fluidic lens, we chose the EL-10-30 electrical lens [www.optotune.com] as a candidate which has a <10 ms response speed.

The techniques described above enable the creation of a MRFL technology that captures a high-definition (HD), wide-angle image of the abdominal cavity. For example, in one possible embodiment, the wide-angle probe of a MRFL system captures an image of approximately an area of 270 mm×200 mm at a 200 mm working distance, with a spatial resolution around 200 µm. The probe will simultaneously capture an HD image of a foveated area with a magnification at least 4 times higher than the wide-angle probe. The covered area of the foveated probe varies with optical magnification, approximately 120 mm×70 mm at 4× area magnification or 80 mm×40 mm at 9× area magnification at a 200 mm working distance. At the same working distance, the spatial resolution of the foveated probe varies from roughly 60 µm to 30 µm, which are sufficient for visualizing minute details such as renal veins. The total diameter of the MRFL probe is about 10 mm, fitting into a laparoscopic trocar. Other tube diameter such as 5 mm is also feasible. The overall length of the probe is adjustable roughly from a 150 mm short scope for SPA technique to a 450 mm long scope for traditional laparoscopic techniques. Although the MRFL concept may be applied to many surgical applications, our prototype is suitable for, but not limited to, nephrectomy and other laparoscopic procedures with similar instrument requirements, with a particular target for SPA-type techniques.

Light Source

If the light source is a 300-W xenon lamp coupled through fiber cables into the scope and delivered to a surgical field via fiber bundles surrounding the optics tube, this commercial source is unable to adequately and uniformly illuminate a large surgical area and produce adequately bright images. Several factors contributed to the light deficiency problem. (1) Due to a longer WD (i.e. 120 mm) than that of a standard laparoscope (SL) (~50 mm), the wide-angle probe captures a much larger area than that of a SL. The commercial light source, limited by the numerical aperture (NA) of the fiber bundles, is unable to adequately and uniformly illuminate such a large area. This factor plays a larger role in the MRFL system with a much longer WD (e.g. ~200 mm) for a low-profile implementation. (2) Assuming the same entrance pupil diameter (EPD), the object-space NA of the MRFL system would be much smaller than that of a SL due to the large WD difference. Consequently, the throughput, which is the product of the imaged area in object space and the subtended solid angle of the optics aperture, of the foveated probe in the MRFL system at a 200 mm WD would be ¼ of the throughput of a SL at a 50 mm WD, assuming the same EPD and equivalently the same field coverage. If adequately illuminated, the throughput of the wide-angle probe imposes less a problem due to its increased field coverage. (3) The dual-view MRFL design necessarily requires splitting the light between the two probes, causing further light attenuation. Assuming the same EPD and a 50/50 beam splitting ratio, the actual irradiance received by the foveated sensor is about ⅛ of that by a SL instrument.

For the MRFL system with a long WD, we address the light deficiency challenge by combining three different mechanisms. (1) Designing a high-efficiency light source using high-power LEDs allows the capability of adequately illuminating the FOV of the wide-angle probe. (2) lowering the F/# of the objective optics, which effectively increases the system throughput for both probes; (3) an uneven beamsplitting ratio such as 10/90 is used to compensate for the fact that the throughput of the wide-angle probe is several times of the foveated probe due to the magnification ratio.

Figure 2:
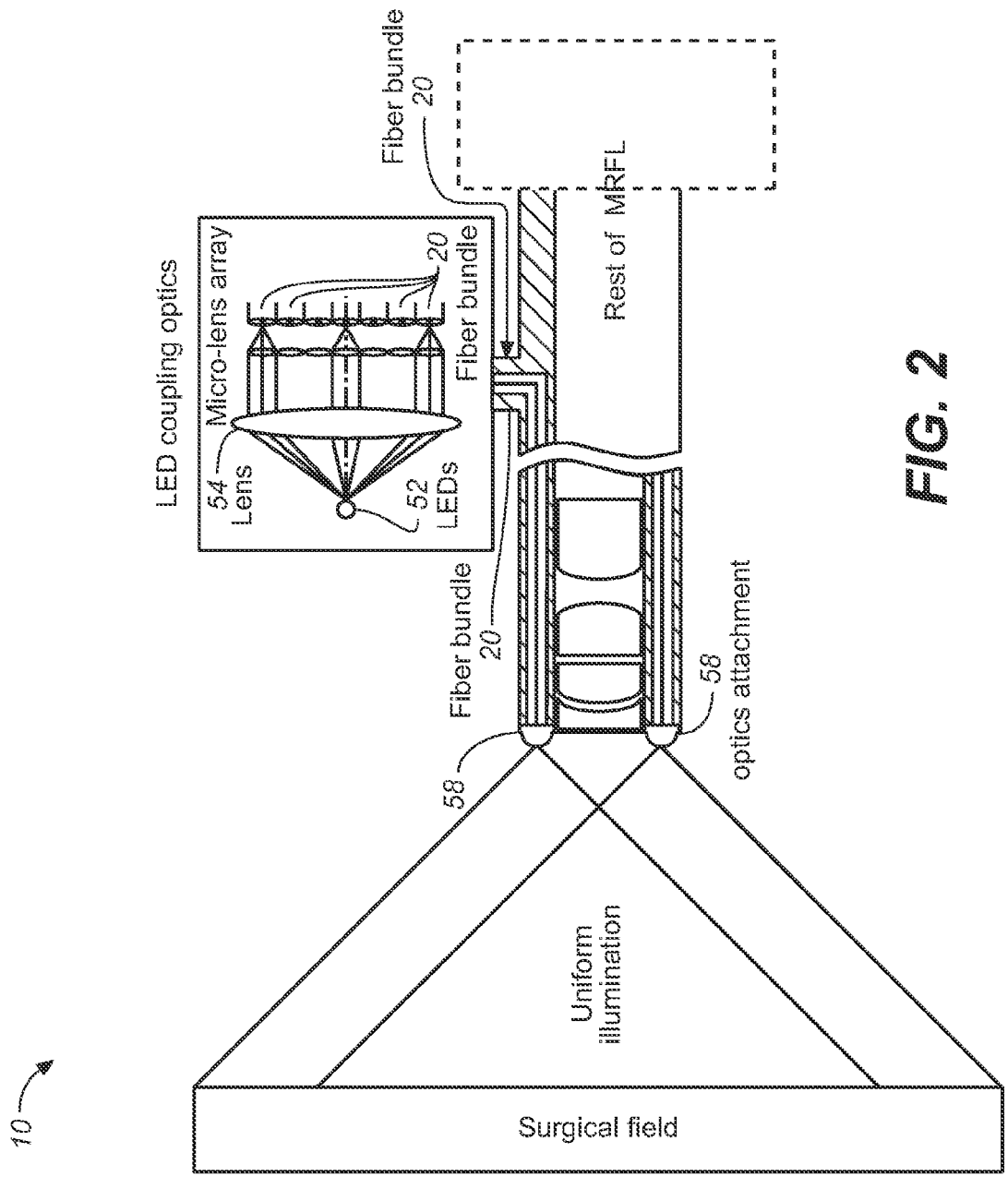
FIG. 2 is a schematic view of the laparoscope of FIG. 1A illustrating an embodiment of the illumination optics of the laparoscope based on light-emitting diodes.

The standard fiber source suffers a low coupling efficiency for transporting light from the lamp source to the surgical field, thus requiring a very strong lamp source (~20,000 lux). We developed a high-efficiency method of illumination with high-power LEDs. This is illustrated in FIG. 2. The light source includes an array 52 of LEDs. Light emitted by the array is collimated first by lens 54 and then focused by a microlens array 56 to the fiber bundles 20.

The new illumination design has two key features: (1) a freeform optical element 58 attached to the end of the fiber bundle 20 surrounding the optics tube to increase the effective numerical aperture (NA) and illumination uniformity across a large area and (2) a microlens-array 56 based high-efficient optics directly coupling LED light into the fiber bundle. To maintain compatibility with SL for comparative studies, the mechanical interface with the LED lighting unit is compatible with the fiber cable for lamp-based sources. At a 200 mm WD, the LED-based illumination will be able to adequately illuminate a surgical field twice as large as a standard source at the same distance. By eliminating the low-efficiency fiber-cable for source coupling, the LED-based illumination method has much higher light transport efficiency from the source to the surgical site. Preliminary analysis suggests that ~500 lux of source illumination would be sufficient, which is nearly 40 times less than the standard source (i.e. ~20,000 lux). The greatly increased light efficiency allows the use of high-power LEDs as the sources.

Figure 3:
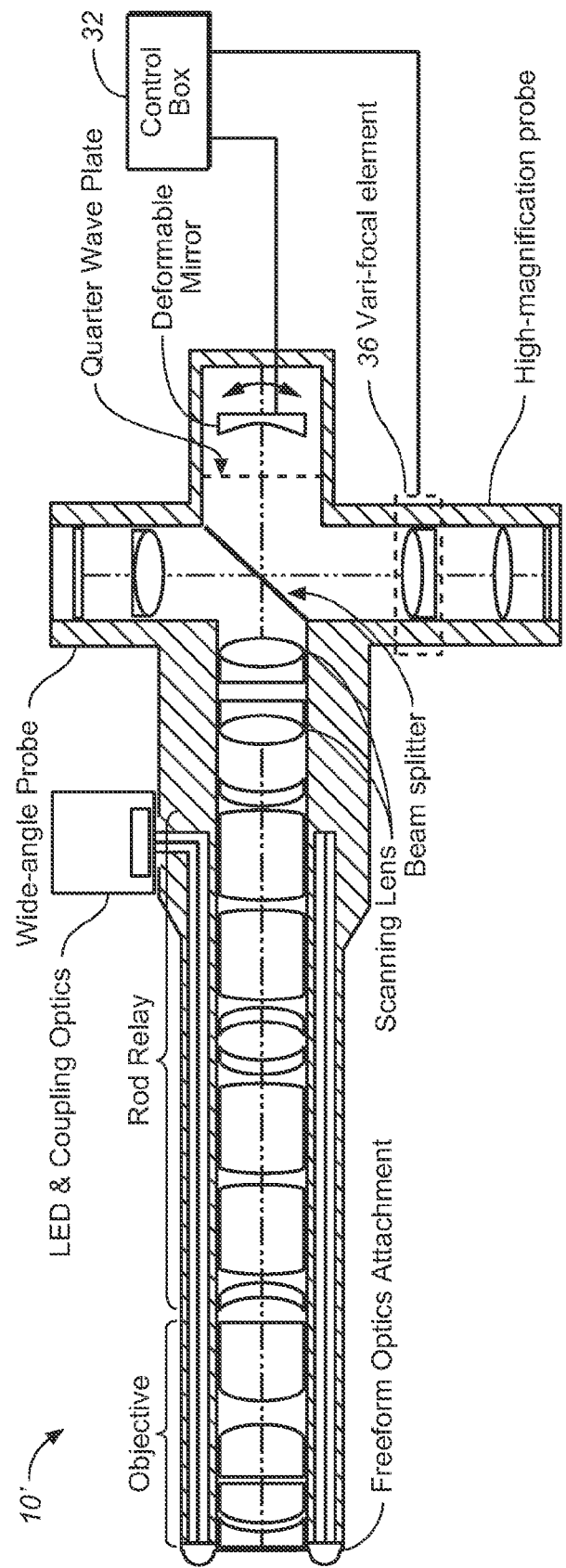
FIG. 3 is a schematic view of a laparoscope to illustrate a second embodiment of the invention.

Instead of using a scanning mirror and variable focal length element as in FIG. 1A, the zooming function may be accomplished by means of a deformable mirror 62 mounted on a scanning platform (not shown in FIG. 3) as illustrated in FIG. 3. The 2D scanning motion of the scanning platform is controlled by a control signal from control device 32. The deformation of mirror 62 is controlled separately by another signal from control device 32. A control voltage from control device 32 controls the focal length of element 36 to compensate the image plane shift due to the deformation of mirror 62 to maintain a fixed object-detector conjugate. Other than this difference, the MRFL 10' of FIG. 3 is the same as and operates in the same manner as that of FIG. 1A.

Figure 4:
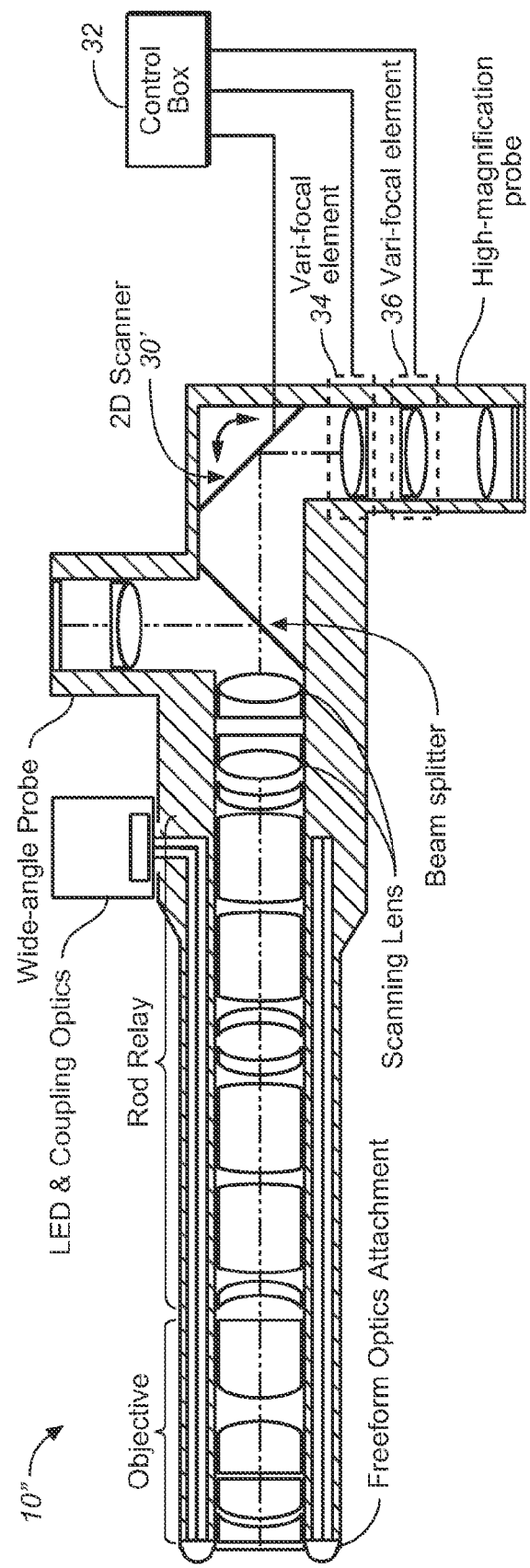
FIG. 4 is a schematic view of a laparoscope to illustrate a third embodiment of the invention.

FIG. 4 illustrates another embodiment MRFL 10" which is substantially the same as the one in FIG. 1A, except that the 2D scanner 30' is oriented to reflect light at an angle towards the probe 18, without being again reflected by the beam splitter 24.

Figure 5:
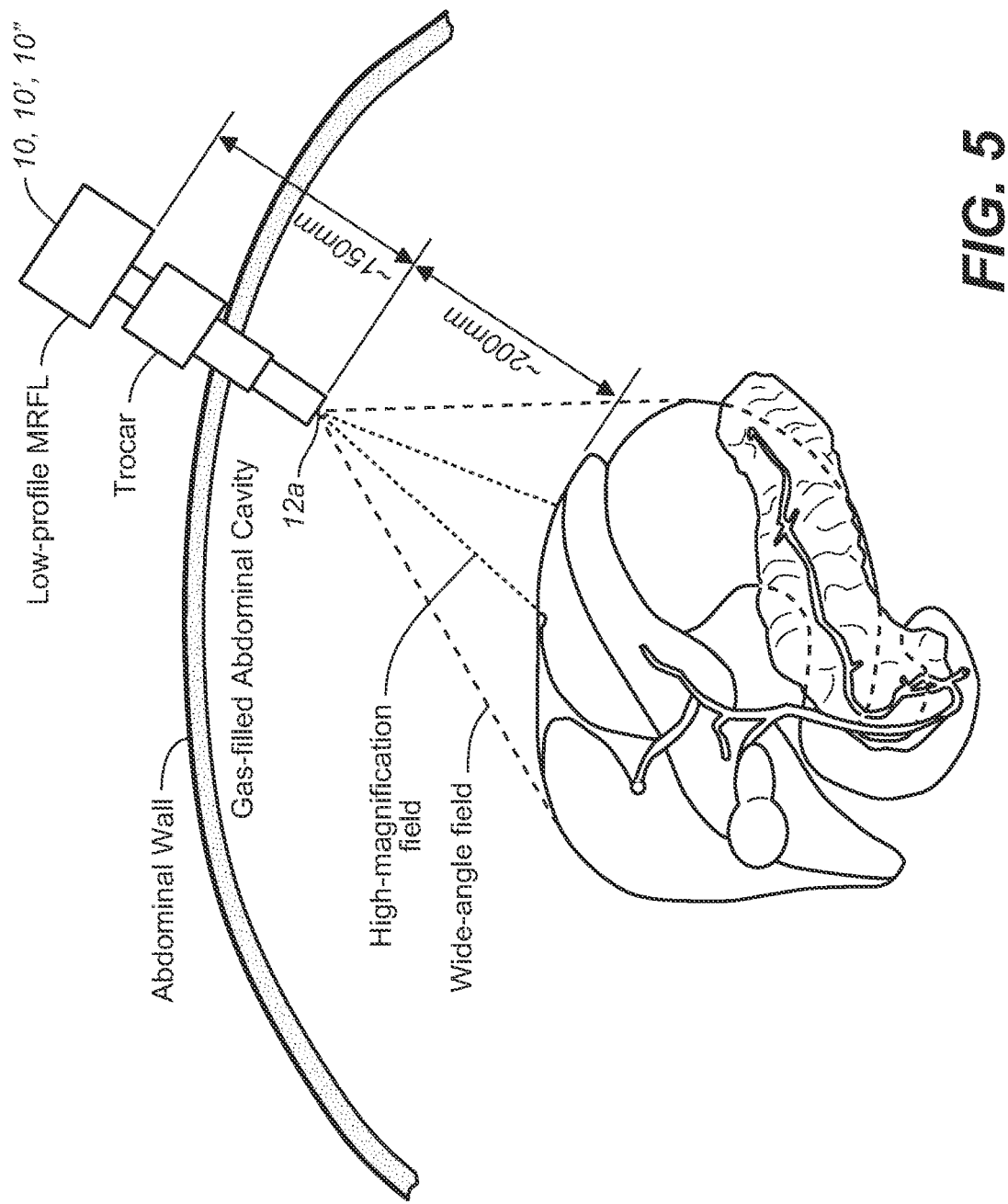
FIG. 5 is a schematic illustration of a clinical application of the laparoscope of the above embodiments.

FIG. 5 is a schematic layout of the MRFL technology for MIS applications. As illustrated in FIG. 5, when any one of the MRFL 10, 10', 10" is used in surgery, the distal end 12a of the inserting tube may be located at a distance of 200 mm from the area of interest, such as an internal organ to be operated on. Even when the laparoscope is at such distance from the area of interest, the surgeon is able to obtain a highly magnified view of the area being operated on while achieving a wider angle stadium view of the body cavity, compared to that of SL. This is in comparison with the performance of SL, where to gain a similar magnification, the distal end would need to be about 50 mm from the area being operated on with a much reduced wide angle FOV. FIG. 5 shows a low profile MRFL where the inserting tube is about 150 mm in length. Alternatively, when a longer MRFL is used, such as one where the inserting tube is about 300 to 400 mm long, the distal end may be inserted further to be 50 mm from the area of interest. In such event, the magnification achieved may be many times that achievable by SL at the same distance of 50 mm from the ROI, while achieving a much wider wide angle stadium view of the body cavity, compared to that of SL.

Implementations

A dual-view MRFL prototype was designed and implemented. With only two image sensors 16a, 18a (1280×960 pixels), the prototype achieves a spatial resolution of ~50 um in the object space. The wide-angle probe 16 captures an 80° FOV and the high-resolution probe 18 covers a 26° FOV of interest. The shared objective lens group 14a and the relay lens groups 14b were assembled in a standard 10 mm diameter rigid scope package. Both objective lens group of F/2.5 and the relay lens groups of magnification −1 were designed to be telecentric in image space. A two-dimensional scanning mirror was placed at an intermediate pupil of the scanning lens group. The anticipated beamsplitting effect on light attenuation was partially compensated by the fact that the F/2.5 objective lens has nearly 2.5 times light collection capability as much as a typical F/6 objective lens in most SLs. Overall, the ratio of the optical power of the two probes is 3 to achieve high-magnification for the foveated probe. In the current MRFL prototype, we substantially reduced the F/# of the objective optics 14a to 2.5 from the typical F/7 in most standard scopes. The reduced objective F/# effectively improves the system throughput and makes the irradiance received by the foveated sensor at a 120 mm WD nearly half of the irradiance received by a SL.

Before the custom-design of the optical system for our MRFL prototype, we built a bench prototype using a commercial laparoscope, off-the-shelf lenses, a MEMS optical scanner for scanner 30 and two color CCD sensors (⅓ inch, 640*480 pixels) for sensors 16a, 18a. The off-the-shelf scope was measured which has an exit pupil diameter of 1.76 mm, located 2.2 mm behind the last surface of the eyepiece. The field angle of the eyepiece is +/−7.06 degrees.

Based on these parameters, we designed additional optical systems to achieve foveation capability. We chose a 50 mm plano-convex lens as L1, the same plano-convex lens as the field lens L2. We further chose a 50 mm achromatic doublet as the scanner lens. The intermediate image is located at the front focal plane of the doublet, so that a MEMS mirror is placed at the relayed pupil position to achieve the scanning function. With these lens combinations, the FOV of the peripheral image is the same as the original scope, while the FOV of the foveated imager is ¼ of the peripheral imager. The overall system allows a 4× magnification by the foveated imager over the peripheral imager. The MEMS scanner enables the function of foveation across the peripheral imager.

The bench prototype described above preliminarily validated the basic functions of the MRFL system. However, the off-the-shelf optics limited the optical performance and prevented us from implementing more advanced imaging capabilities. We continued the research by performing a fully custom system design and optimization. We started with a detailed analysis of the medical applications and mapped the requirements into system performance metrics. We then performed an overall first-order design based on choices of key optical component or subsystems, followed by custom design of the objective lens group, the rod relay lens group, the foveated probe, and the peripheral probe. The optical performances of the optimized sub-systems and integrated system were fully simulated and analyzed. Tolerance analysis was performed for fabrication preparation. The optical mechanical housing units and lens assembly units were designed. Both the optical systems and opto-mechanical units were prototyped.

First-order System Design

In this first-order design of the custom MRFL system, the foveated and peripheral imager share the same objective, rod relay lenses, and a scanning lens. One of the key constraints to the objective and rod relay lenses is that their diameters need to be less than 6 mm to achieve a final package of 10 mm scope for laparoscopic applications. Moreover, the objective lens is required to be strictly telecentric in its image space so that the diameter of the rod lens relay system could be reduced. Another critical constraint is the F/# of the objective lens, which determines the overall light throughput as well as the resolution of the system. The third constraint relates to the effective aperture and scanning range of the MEMS scanner. Our MEMS scanner prototype has a 10-mm usable aperture and a 5-deg mechanical scanning capability along a single axis. These parameters require a careful choice of the focal lengths for the scanning lens and objective lens. The fourth constraint relates to the clear aperture (2.5 mm) of the available liquid lens which we intend to use for further magnification control. The fifth constrain is to achieve at least 9× optical magnification between the foveated and peripheral imager, which requires the foveated probe covers no more than ⅓ of the objective FOV in both horizontal and vertical directions. Finally, we require the overall length of the rod relay lens can be flexibly configurable so that we can configure the integrated MRFL system into different physical profiles (for example a low-profile probe with a length as long as 150 mm or a regular-length probe with a length as long as 450 mm). Due to this unique requirement on the rod relay system, we divide the rod relay into as many as 4 groups, each of which is required to achieve a unit magnification and to be strictly telecentric in both object and image spaces so that when the number of relay groups to be used can be flexible.

Based upon these systematic constraints discussed above, we chose the following first-order optical configurations:

$f_{obj}=2$ mm; HFOV=40°; $D_{stop}=0.8$ mm

The height of the intermediate images created by the objective and relay groups is:

$h_{int.img}=f_{obj} \times \tan(HFOV)=2 \times \tan 40°=1.6782$ mm

The diameter of the objective lens ($D_{obj}$ no vignetting) is $D_{obj}=2 \times f_{obj} \times \tan(HFOV)+D_{stop}=2 \times 2 \times \tan 40°+0.8=4.1564$ mm The effective pupil diameter at the surface of MEMS tilting mirror ($D_{pupil\ at\ tilting\ mirror}$):

$$D_{Pupil\ at\ tilting\ mirror} = \frac{f_{scan}}{F/\# \text{ of the objective lens}} = \frac{f_{scan}}{f_{obj}} \times D_{stop} = \frac{f_{scan}}{2.5} < 10 \text{ mm}$$

The maximum mirror tilting angle ($\beta$) is given by $$\beta = \frac{1}{2}\tan^{-1}\left[\frac{f_{obj}}{f_{scan}} \times \tan\left(\frac{2}{3} \times HFOV\right)\right] = \frac{1}{2}\tan^{-1}\left[\frac{2}{f_{scan}} \times \tan\left(\frac{2}{3} \times 40°\right)\right] < 2.5°$$

Therefore 11.48 mm < $f_{scan}$ < 40 mm

Considering the size and performance balance, we chose $f_{scan}=14$ mm

The focal length of the foveated relay lens $$f_{foveated\ relay} = \frac{D_{CCD}/2}{\tan\left(\frac{1}{3} \times HFOV \times \frac{f_{obj}}{f_{scan}}\right)}$$

By choosing a ¼ inch CCD sensor for the foveated imager (DCCD=4 mm), the focal length of the foveated lens system is 60 mm. We chose the same CCD sensor for the peripheral imager, thus the focal length of the peripheral relay is 19.99 mm given by the following equation $$f_{peripheral\ relay} = \frac{D_{CCD}/2}{\tan\left(HFOV \times \frac{f_{obj}}{f_{scan}}\right)}.$$

TABLE 1

First-Order System Specifications and Performance Metrics

| Parameter | Value |
| --- | --- |
| Shared objective lenses (Integrated into a rigid tube with a diameter of 10 mm): | |
| FOV | 80° diagonal, or 67.74° (W) × 53.44° (H) |
| Working distances (WD) | 90~180 mm |
| Visual field size | 100 mm × 75 mm (80 mm WD)~250 × 180 mm (180 mm WD) |
| Optical system aperture diameter | <6 mm |
| F/# and Numerical Aperture (NA) | F/2.5 |
| Focal length | 2 mm |
| Modulation Transfer Function (MTF) | >20% @ 450 lps/mm |
| Distortion | <15% at the edge field |
| Telecentricity | object space telecentric to ensure constant optical magnification at different working distances |
| Shared rod relay lenses (Integrated into a rigid tube with a diameter of 10 mm): | |
| FOV | Same as the image size of the objective lens |
| Working distances (WD) in objective space | Same as the objective lens |

TABLE 1-continued

First-Order System Specifications and Performance Metrics

| Parameter | Value |
|---|---|
| Optical magnification | 1:1 |
| Optical system aperture diameter | <6 mm |
| F/# and NA | NA = 0.2 |
| Overall length | Versatile, ~150 mm (low profile scope) to 450 mm (long profile) |
| MTF | >20% @ 480 lps/mm |
| Distortion | <0.00001% at the edge field |
| Telecentricity | Strict double-space telecentricity to enable the versatility of the relay system by concatenating multiple groups of the same rod lenses |
| Wide FOV Probe (Additional imaging optics is needed besides the shared the objective and relay lenses): | |
| FOV | Same as the objective lens |
| Visual field size | Same as the objective lens |
| Detector resolution, pixel size and array size | ⅓ inch CCD; resolution 1280*960; pixel size 3.75 um*3.75 um, |
| Detail resolvability at the object space | 150 μm (80 mm WD)~3150 μm (180 mm WD) |
| Image Space NA | F/3.6 |
| MTF | |
| Distortion | <15% |
| Telecentricity | Not required |
| Foveated FOV Probe (Additional optical scanner, liquid lens, and other lens group are added): | |
| FOV | ~±13° (Diagonal) (9× area magnification) |
| Visual field size | 33 × 25 mm (80 mm WD, 9×)~80 × 60 mm (180 mm WD, 9×) |
| Detector resolution, pixel size, and array size | ⅓ inch CCD; resolution 1280*960; pixel size 3.75 um*3.75 um, |
| Detail resolvability at the object space | 50 μm (80 mm WD, 9×)~105 μm (180 mm WD, 9×) |
| Foveated-field scanning speed | <100 ms across the entire field |
| MTF | >0.2 @ 80 lp/mm |
| Distortion | |
| Telecentricity | Not required |

Optical Design

Figure 6:
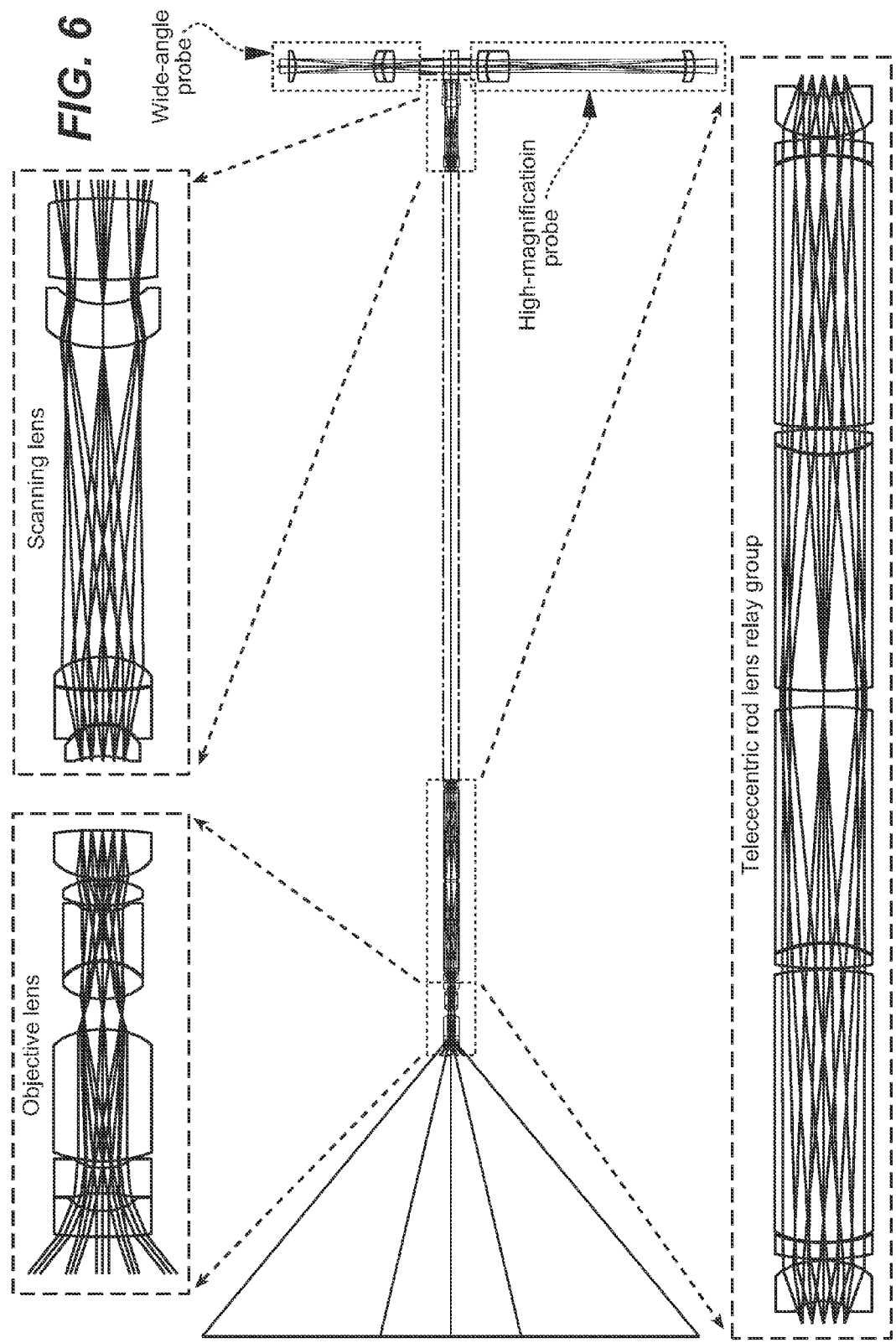
FIG. 6 is the optical layout of a portion the laparoscope of FIG. 1A illustrating in more detail the collection optics subsystem of the laparoscope.

FIG. 6 demonstrates the custom-designed optical system for the MRFL prototype, with its key specifications listed in Table 1. It consists of a shared F/2.5 objective lens group, multiple shared relay lens groups, a scanning lens group, a wide-angle imaging probe and a high-resolution foveated imaging probe. The shared objective lens group and the relay lens groups were assembled in a standard 10 mm diameter rigid scope package. To fit this standard package, the diameters of these lenses need to be less than 5.7 mm. The objective lens group 14a includes 5 elements, offers a 80° diagonal FOV with a diffraction limited performance. It was designed to be telecentric in image space. The relay lens groups were designed to be telecentric in both object and image space and each relay group works at a magnification of −1. To reduce fabrication cost, each of the relay groups was designed to be identical, and the left and right portions within each relay group are symmetric. The rod relay lens component 14b offers a 1:1 relay. Each rod lens group may have a total length of 150 mm. The telecentricity of the objective and relay groups enables that a flexible number of relay lens groups of limited diameter can be concatenated to extend the instrument length, without noticeable degradation of image quality, to create laparoscopes of different length profiles. It makes the instrument versatile for from low profile (e.g. with the inserting tube 100 to 250 mm in length) to long scope. For the low profile MRFL, one or two groups of relay lens may be included. The wide-angle probe 16 covers the same FOV as the objective lens. For the normal profile MRFL, two to four groups of relay lens may be included. The wide-angle probe 16 covers the same FOV as the objective lens. A relay lens group is required to image the field onto the size of a selected ⅓" image sensor. The high-magnification foveated probe 18, covers a 26-degree FOV (i.e. ⅓ of wide-angle probe).

The scanning lens group works like an eyepiece with a two-dimensional scanning mirror placed at the exit pupil. A polarizing beamsplitter (PBS) along with a quarter wave plate is inserted between the scanning lens and the mirror for splitting the light paths for the wide-angle and high-resolution probes. The PBS directs the s-polarized light into the wide-angle imaging probe and p-polarized light into the high-resolution imaging probe. Although a PBS and a quarter wave plate were used to improve the light efficiency, compared to a standard single-view laparoscope, only half of the collected light goes into the high-resolution probe and the other half goes into the wide-angle probe. The anticipated light splitting effect was compensated by the fact that the F/2.5 objective lens has twice light collection capability as much as a standard F/4 objective lens. Moreover, the lower F-number objective lens provides better resolution.

The optical system design of the MRFL system was quite challenging due to the limited lens diameter, large FOV, telecentric requirements, and low F-number. The objective lens was designed to have a focal length, $f_{obj}$, of 2 mm and have diffraction limited performance with less than 17% distortion. The length of each relay group is 80 mm. Each group has a symmetric configuration to take advantage that the odd order aberrations such as distortion, coma and lateral chromatic aberration are cancelled out. Each group was well optimized with diffraction limited performance so that the image quality won't degrade much when the number of relay groups increases.

The scanning lens group requires a long exit pupil distance (EPD) to accommodate the PBS and wave plate. The focal length of the scanning lens, $f_{scan}$, is 14 mm while the EPD is 16 mm. However, one problem is that as the number of relay groups increases, the spherical aberration and the longitudinal chromatic aberrations accumulate. In order to correct those accumulated aberrations through multiple relay groups; we apply a diamond-turned plastic hybrid lens in the scanning lens group. One surface of the plastic lens has a diffractive optical element (DOE) and the other surface is aspheric. The DOE has the opposite dispersion compared to the refractive lens, so that the longitudinal chromatic aberrations can be balanced. The aspheric surface corrects the higher order aberrations. The plastic lens was placed near the intermediate pupil to effectively balance those accumulated aberrations.

Both the wide-angle and high-resolution imaging probes use simple optics. The wide-angle probe consists of a doublet and a field lens; and the high-resolution probe has two singlets and a field lens. The focal length of the wide-angle imaging probe is 30 mm, while that of the high-resolution imaging probe, $f_{high-res}$, is 90 mm.

By controlling the tilting angle of the scanning mirror, the high-resolution probe can be engaged to any subfield of the entire surgical area. Assuming the high-resolution probe is aiming at θ° in the entire FOV, the tilting angle of the scanning mirror, β°, is given by.

$$\beta = 0.5 \times (f_{obj}/f_{scan}) \times \theta \quad (1)$$

In our prototype design, the maximum tilting angle required is 1.9° to cover the full FOV. A motorized gimbal mirror mount (Zaber T-OMG Series) was used, which has a tilting range of ±7°, the maximum speed of 7°/sec, and a minimal scanning step of 0.0001°. The mirror enables the ability to scan across the entire surgical field in less than 0.4 seconds and fixating the position of the high-resolution probe in an accuracy of 0.097 mm.

The MRFL was optimized at the working distance of 120 mm with a depth of field from 80 mm to 180 mm. The corresponding surgical field is about 80×60 mm² at an 80 mm working distance and 240×180 mm² at 180 mm distance, respectively. For the high-resolution probe, of which the FOV is ⅓ of that of the wide-angle probe, the visual surgical field is 27×20 mm² at 80 mm working distance and 80×60 mm² at 180 mm working distance.

Figure 7:
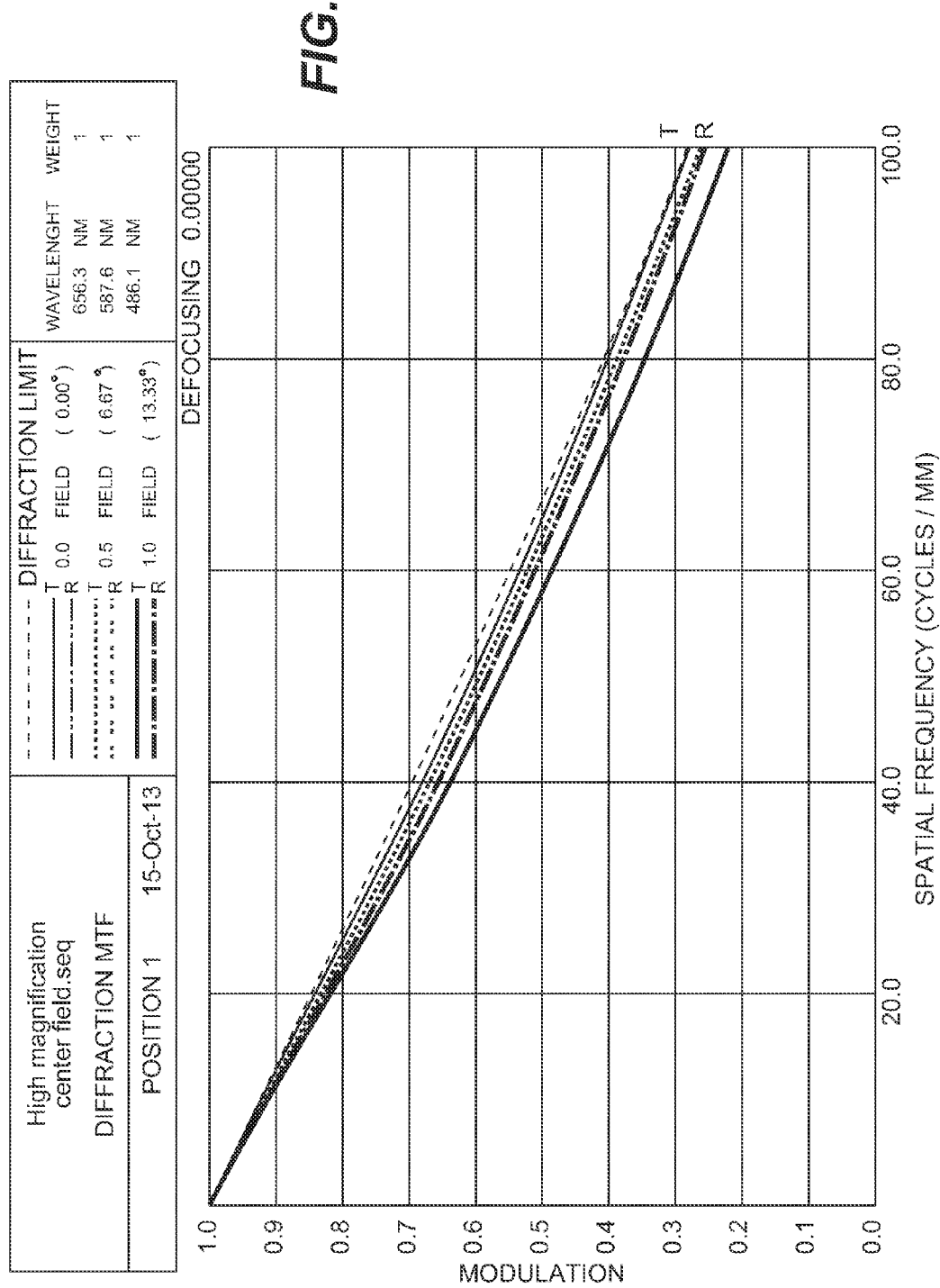
FIG. 7 is a graphical illustration of the modulation transfer functions of the high magnification probe of the laparoscope in the above embodiments foveated on the central field.

In the prototype we used ⅓" color CCD sensors (PointGrey DragonFly2 DR2-13S2C-CS) for both imaging probes. The pixel resolution of the sensors is 1280×960, and the color pixel size is 7.5 um×7.5 um. The spatial resolvability of the high-resolution probe is given by $$D = 7.5 \text{ um}/(m_{high-res} \times m_{obj}) \quad (2)$$

Where $m_{obj}$ and $m_{high-res}$ are the magnifications of the objective lens and the high-resolution imaging probe, respectively. At a giving working distance, L, they are calculated by $m_{obj} = -f_{obj}/L$ and $M_{high-res}/f_{scan}$, respectively. The spatial resolvability of the high-resolution probe is 46.67 um, 70 um, and 105 um, corresponding to a spatial frequency of 10.7, 7.1, and 4.81 ps/mm, at a working distance of 80 mm, 120 mm, and 180 mm, respectively FIG. 7 shows the MTF performance of the foveated high magnification probe 18. The overall foveated imager has no more than 2% of distortion. The optical performance of a system with a 4-group rod relay system has similar optical performances.

Figure 8:
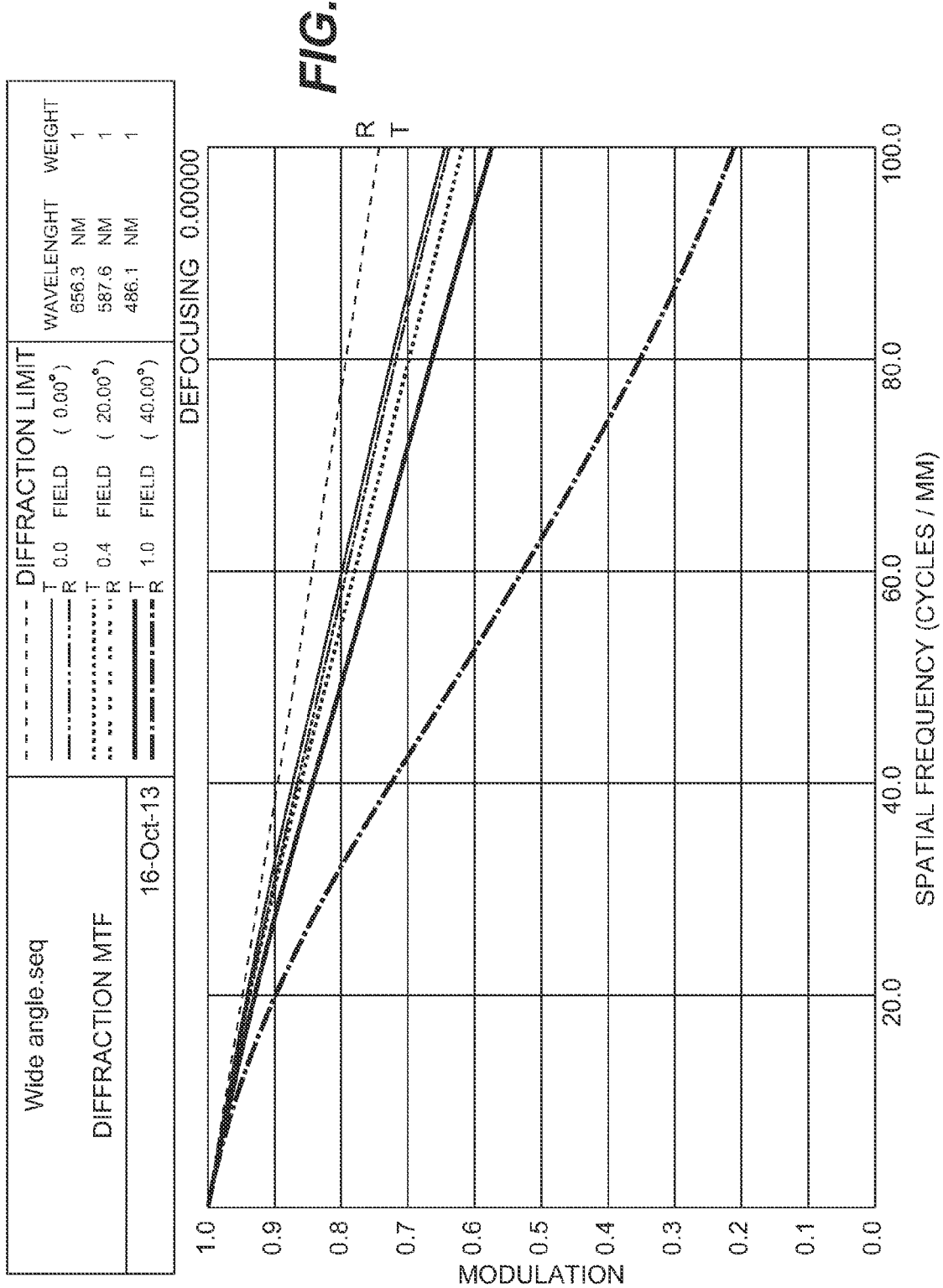
FIG. 8 is a graphical illustration of the modulation transfer functions of the wide angle probe of the laparoscope in the above embodiments across the entire field of view.

Besides the objective and rod relay lenses, the peripheral imager requires an additional lens group to form a wide-FOV imager while also sharing the same scanning lens as the foveated imager. However, the additional lens group only requires a doublet. FIG. 8 shows the MTF performance of the wide angle probe 16 across the entire FOV. Overall, the peripheral imager covers the entire FOV of the objective FOV. The overall peripheral imager has no more than 20% of distortion. The optical performance of a system with a 4-group rod relay system has similar optical performances.

Additionally, the overall optical systems were optimized for good performance across a large range of working distance between 80 mm and 180 mm.

FIG. 9 shows two integrated prototypes of different length profile scope: a normal profile and a low profile. In the low profile scope, the inserting tube 12 has a length in the range of about 100 to 250 mm. In the normal profile scope, the inserting tube 12 has a length in the range of about 300 to 400 mm. The normal profile package has four relay groups and the low profile package has two relay groups. The telecentricity of the objective and relay groups enables that a flexible number of relay lens groups of limited diameter can be concatenated to create laparoscopes of different length profiles. In the prototypes, two ⅓" CCD sensors (DR2-13S2C-CS by PointGrey), with 1280×960 pixels and color pixel size of 7.5 um, were used. A motorized gimbal mirror mount (Zaber T-OMG Series) was used to enable the ability to scan across the entire surgical field in less than 0.4 seconds in a positional accuracy of 0.1 mm.

Resolution Test

The MRFL optics was optimized at a 120 mm WD but with a working range of 80-180 mm, within which the modulation transfer function (MTF) values of both the wide-angle and high-resolution probes are greater than 0.2 at the cut-off frequency of the image sensors. We adopted a US1951 resolution target and a slanted edge technique to evaluate the spatial resolution and MTF of our prototype. We further compared against a standard laparoscope. We quantified the FOV of the dual-view probes as well as the scanning range and speed of the foveated probe. The SL utilized for comparison captures an area of ~56×42 mm² at a typical 50 mm WD, with a resolution of ~2 lps/mm in the object space. At a 80 mm WD, the wide-angle and high-resolution probes capture a surgical field of ~106×80 mm² and 30×22 mm², respectively, and the foveated probe yields a 10 lps/mm resolution, 5 times as good as the SL under comparison. At a 180 mm WD, the two probes capture an area of about 240×180 mm² and 68×50 mm², respectively. The wide-angle probe captures an area 16 times as large as that of the SL (at 50 mm WD), and the foveated probe yields a 41 ps/mm resolution, twice as good as the SL under comparison. With an ISO 12233 camera test target placed at 180 mm.

Our current MRFL prototype uses a simple graphical user interface (GUI) by OPEN CV and MFC to properly display the video sequences acquired simultaneously by the foveated and peripheral probes. By simply clicking the "start" button, the program turns on the two cameras or imaging sensors 16a and 18a, or clicking the "STOP" button to turn off the cameras. A user may select a region of interest (ROI) in the peripheral window by simply clicking the left button of a mouse, the selected ROI is used to steer the MEMS mirror in the foveated camera to capture a high-magnification view of the selected region. The high-resolution video captured by the foveated camera is displayed in a separate window on the right. Meanwhile it is also overlaid at the corresponding position in the peripheral window to enhance context awareness. For debugging purpose, the video contents shown in the GUI interface are irrelevant to endoscopic application and the foveated camera was pointing to a direction different from the peripheral imager. Once the custom-designed probes are prototyped, they will be integrated with this interface.

We further developed an image processing suite to perform two types of functions, ROI tracking and image synthesis and enhancements. First, in our current MRFL prototype, a keypad-based interface was provided to allow a user to manually select a ROI for the foveated probe. Such manual control method, however, fails to respond to a change of interest in real time. More importantly, a hand-based interface is not clinically practical unless a dedicated camera assistant is expected. Failure to provide easy-to-use and reliable interface will hamper the adaptation of the probe in clinical applications. We propose three different methods for steering the foveated probe.

Figure 11:
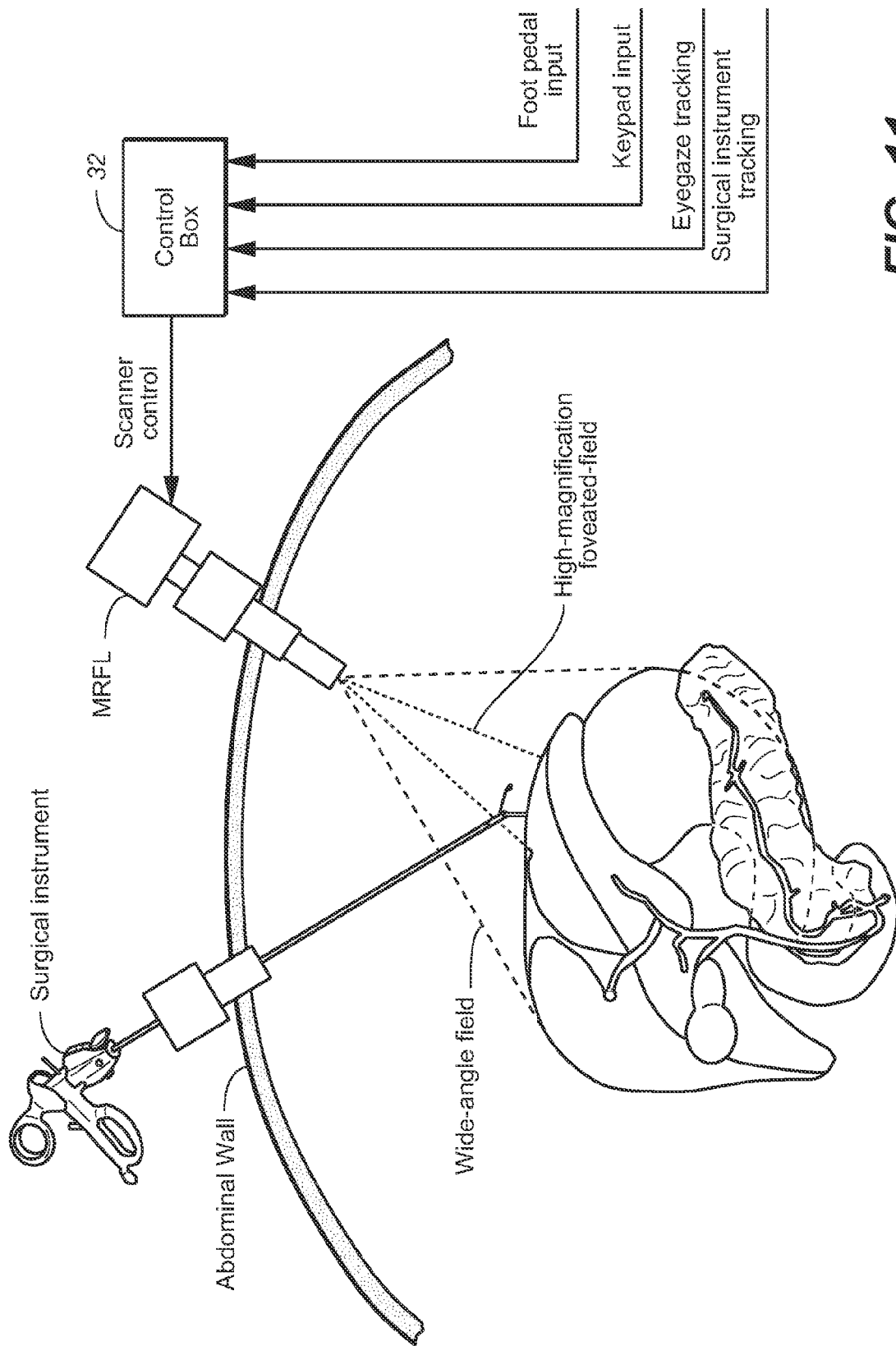
FIG. 11 is a schematic illustration of a clinical application of the laparoscope of the above embodiments to illustrate a method of control of foveation.

These methods are illustrated in FIG. 11. The first is a foot-pedal based method where the surgeon is provided an easily accessible foot pedal for directly controlling the foveation direction and optical magnification based on his or her specific needs. Foot-pedal method has already been clinically used in robotic surgery and may be adapted for steering the foveated probe. Thus, the control device 32 receives an input signal from a control instrument (not shown) that has a foot pedal input. The second method is an automatic tracking method based on image analysis algorithms that will identify and locate landmark features from the context view captured by the wide-angle probe. In this method, the image analysis algorithms will provide guidance to an operator who then sends a control signal to control device 32 by inputting through a keypad of a control instrument (not shown) such as a computer. Surgical instruments may provide reliable features for tracking purpose. Features of the surgical sites, such as specific organs under operation, may also be used for tracking Thus, it is possible for the control signal to control device 32 to be generated automatically by a control instrument (not shown) that tracks a surgical instrument or surgical site. The third method is an automatic tracking method based on image analysis algorithms that will track the gaze direction and fixation of the surgeon on the wide-angle image display. An eyetracking camera (not shown) will be installed next to the monitor (not shown) displaying the wide-angle images and gaze point can thus be detected when the surgeon is attending the wide-angle image. The combination of foot-pedal and automated ROI tracking methods will enhance interface robustness and accuracy. In scenarios where reliable features are hard to detect, automated tracking methods may be less efficient and robust due to feature tracking and image analysis errors.

While the invention has been described above by reference to various embodiments, it will be understood that changes and modifications may be made without departing from the scope of the invention, which is to be defined only by the appended claims and their equivalents. For example, while the embodiments described herein refer to laparoscopes, the same features may be used for other devices such as endoscopes or other devices for insertion into and viewing areas of interest in human and animal bodies. Such and other variations are within the scope of the invention.

What is claimed is:

1. An endoscope comprising:
   an inserting tube having a viewing end and a distal end, said distal end suitable to be inserted into a human body to a location next to a region in the human body to be viewed;
   a first optical system in said inserting tube for transmitting light originating from said region from said distal end towards said viewing end;
   a second optical system at or near the viewing end that splits the light transmitted by the first optical system along two different first and second optical paths;
   a first imaging probe in the first optical path for imaging said region at a first field of view and at a first magnification; and
   a second imaging probe in the second optical path for imaging a subregion in said region at a second field of view that is smaller than the first field of view and at a second magnification that is higher than the first magnification, said second optical system including a beam splitter and a light reflective element, wherein said beam splitter is a polarizing beam splitter, and said second optical system further including a quarter wave plate.

2. The endoscope of claim 1, wherein said light reflective element reflects light from the beam splitter through said quarter wave plate towards the beam splitter which in turn reflects a portion of the light from the light reflective element towards one of the two probes.

3. The endoscope of claim 1, wherein the inserting tube has a length in a range of substantially 100 to 250 mm.

4. The endoscope of claim 1, wherein the inserting tube has a length in a range of substantially 300 to 400 mm.

5. The endoscope of claim 1, wherein the inserting tube includes a third optical path for light to illuminate the region in the human body to be viewed.

6. The endoscope of claim 5, further comprising a plurality of LEDs, said third optical path comprising fiber bundles transmitting light emitted by the LEDs to the region in the human body to be viewed.

7. The endoscope of claim 5, said third optical path comprising optics elements coupled to the fiber bundles at the distal end of the inserting tube for increasing numerical aperture of the fiber bundles and uniformity of illumination of the region in the human body to be viewed.

8. The endoscope of claim 1, wherein said first optical system is substantially telecentric.

9. The endoscope of claim 1, wherein a ratio between the second and first magnifications is greater than 1.5.

10. The endoscope of claim 1, said second optical system comprising a scanning device that scans the light transmitted by the first optical system along the second optical path to locate the subregion anywhere within the region.

11. The endoscope of claim 1, comprising a plurality of LEDs, and wherein
    the second optical system is configured to provide views of said region or a subregion thereof at two different fields of view and at two different magnifications, and
    the inserting tube includes a third optical path transmitting light emitted by the LEDs to illuminate the region in the human body to be viewed.

12. The endoscope of claim 11, said third optical path comprising optics elements coupled to the fiber bundles at the distal end of the inserting tube for increasing numerical aperture of the fiber bundles and uniformity of illumination of the region in the human body to be viewed.

13. The endoscope of claim 11, said third optical path comprising a micro-lens array that focuses light from the LEDs to the fiber bundles.

14. An endoscope comprising:
an inserting tube having a viewing end and a distal end, said distal end suitable to be inserted into a human body to a location next to a region in the human body to be viewed;
a first optical system in said inserting tube for transmitting light originating from said region from said distal end towards said viewing end;
a second optical system at or near the viewing end that splits the light transmitted by the first optical system along two different first and second optical paths;
a first imaging probe in the first optical path for imaging said region at a first field of view and at a first magnification; and
a second imaging probe in the second optical path for imaging a subregion in said region at a second field of view that is smaller than the first field of view and at a second magnification that is higher than the first magnification, said second optical system including a beam splitter and a light reflective element, said light reflective element comprising a scanning mirror or a deformable mirror and a scanning platform.

15. The endoscope of claim 14, said second optical system further including a control mechanism for controlling scanning motion of the scanning mirror or the scanning platform, so as to scan the field of view of the second imaging probe to any subregion within the field of view of the first imaging probe to provide a foveated image of said subregion.

16. The endoscope of claim 15, wherein said control mechanism causes the scanning mirror or the scanning platform to scan in two directions that are transverse to one another.

17. The endoscope of claim 14, said second imaging probe further comprising a variable focal element that changes its focal length in response to a control signal from the control mechanism for autofocusing light from the deformable mirror in the second imaging probe to maintain an object image conjugate plane of the image of the subregion at a fixed location during optical zooming.

18. The endoscope of claim 14, said light reflective element comprising a scanning mirror, said second imaging probe further comprising a first variable focal element that changes its focal length in response to a control signal from the control mechanism for optical zoom.

19. The endoscope of claim 18, said second imaging probe further comprising a second variable focal element that changes its focal length in response to a control signal from the control mechanism for autofocusing light from the first variable focal element in the second imaging probe to maintain an object image conjugate plane of the image of the subregion at a fixed location during optical zooming.

20. An endoscope comprising:
an inserting tube having a viewing end and a distal end, said distal end suitable to be inserted into a human body to a location next to a region in the human body to be viewed;
a first optical system in said inserting tube for transmitting light originating from said region from said distal end towards said viewing end;
a second optical system at or near the viewing end that splits the light transmitted by the first optical system along two different first and second optical paths;
a first imaging probe in the first optical path for imaging said region at a first field of view and at a first magnification; and
a second imaging probe in the second optical path for imaging a subregion in said region at a second field of view that is smaller than the first field of view and at a second magnification that is higher than the first magnification, said second optical system including a beam splitter and a light reflective element, wherein said light reflective element reflects light from the beam splitter towards the beam splitter which in turn reflects a portion of the light from the light reflective element towards one of the two probes.

21. The endoscope of claim 20, wherein said light reflective element reflects light from the beam splitter towards the second imaging probe.

22. The endoscope of claim 20, wherein said beam splitter reflects light towards the first imaging probe, and transmits light that is directed to the second imaging probe.

23. An endoscope comprising:
an inserting tube having a viewing end and a distal end, said distal end suitable to be inserted into a human body to a location next to a region in the human body to be viewed;
a first optical system in said inserting tube for transmitting light originating from said region from said distal end towards said viewing end;
a second optical system at or near the viewing end that splits the light transmitted by the first optical system along two different first and second optical paths;
a first imaging probe in the first optical path for imaging said region at a first field of view and at a first magnification; and
a second imaging probe in the second optical path for imaging a subregion in said region at a second field of view that is smaller than the first field of view and at a second magnification that is higher than the first magnification, said second optical system including a beam splitter and a light reflective element, wherein said beam splitter reflects light towards the first imaging probe, and transmits light that is directed to the second imaging probe, and wherein said beam splitter transmits more light than is reflected by the beam splitter.

24. The endoscope of claim 23, wherein the intensity of light transmitted by the beam splitter is at least 1.5 times that of the intensity of light reflected by the beam splitter.

25. A method for viewing a region in the human body, comprising:
inserting into the human body a tube having a viewing end and a distal end, so that said distal end is located next to a region in the human body to be viewed;
transmitting light originating from said region from said distal end towards said viewing end;
splitting the light transmitted towards said viewing end along two different first and second optical paths;
directing light transmitted along the first optical path to a first imaging sensor for imaging said region at a first field of view and at a first magnification; and
directing light transmitted along the second optical path to a second imaging sensor for imaging a subregion within said region at a second field of view that is smaller than the first field of view and at a second magnification that is higher than the first magnification, to provide a foveated image of said subregion, wherein said region and subregion are imaged at substantially the same time, wherein the light directed to the first and second imaging sensors are polarized.

26. The method of claim 25, wherein the light directed to the second imaging sensor is scanned so as to move the subregion imaged by the second imaging sensor to another location within the region.

27. The method of claim 25, wherein the scanning of the light directed to the second imaging sensor is performed in response to a control signal from a control device having a foot pedal or keypad input, or a control device that generates a control signal that indicates eye gaze direction or location of a surgical instrument.

28. The method of claim 25, wherein the light directed to the second imaging sensor is optically zoomed to change the size of the subregion and the magnification of the image of the subregion.

29. The method of claim 28, wherein the optical zooming is performed by means of a deformable mirror or a variable focal length element.

30. The method of claim 28, wherein the light directed to the second imaging sensor is altered by an optical device to maintain an object image conjugate plane of the image of the subregion at a fixed location during optical zooming.

31. The method of claim 25, wherein a ratio between the second and first magnifications is greater than 1.5.

32. The method of claim 25, further comprising scanning the light directed along the second optical path to locate the subregion anywhere within the region.

* * * * *